(12) United States Patent
Welborn

(10) Patent No.: US 7,628,798 B1
(45) Date of Patent: Dec. 8, 2009

(54) HUB AND HANDLE DESIGN FOR CARPAL TUNNEL RELEASE TOOL

(75) Inventor: Kenneth Welborn, Charlottesville, VA (US)

(73) Assignee: MicroAire Surgical Instruments, Inc., Charlottesville, VA (US)

( * ) Notice: Subject to any disclaimer, the term of this patent is extended or adjusted under 35 U.S.C. 154(b) by 0 days.

(21) Appl. No.: 12/277,682

(22) Filed: Nov. 25, 2008

(51) Int. Cl.
*A61B 17/32* (2006.01)
(52) U.S. Cl. ...................................... 606/170
(58) Field of Classification Search ................. 606/167, 606/170; 403/348, 349; 604/165.01–165.04
See application file for complete search history.

(56) References Cited

U.S. PATENT DOCUMENTS

| | | | |
|---|---|---|---|
| 4,785,805 A * | 11/1988 | Joffe et al. ................... | 606/15 |
| 4,962,770 A | 10/1990 | Agee | |
| 4,963,147 A | 10/1990 | Agee | |
| 5,089,000 A | 2/1992 | Agee | |
| 5,306,284 A | 4/1994 | Agee et al. | |
| 5,407,293 A * | 4/1995 | Crainich ................... | 403/322.1 |
| 5,499,992 A * | 3/1996 | Meade et al. ............... | 606/170 |
| 6,730,081 B1 | 5/2004 | Desai | |

* cited by examiner

*Primary Examiner*—Anhtuan T Nguyen
*Assistant Examiner*—Ryan J Severson
(74) *Attorney, Agent, or Firm*—Whitham Curtis Christofferson & Cook, PC

(57) ABSTRACT

A surgical instrument that includes a probe that is extended into a body cavity and a handle held by a surgeon outside the body cavity, where the surgical instrument includes both an optical system and surgical tool operable by the surgeon that passes through the handle and probe includes a connection configuration on its proximal end of the probe and elements within a bore of the handle which allows for securely locking the probe in at least two different orientations. In particular, the proximal end of the probe includes a pair of axial slots and a twist region which cooperate with inwardly projecting land regions in a bore of the handle. A locking mechanism is used to selectively move a locking member into and out of one or the other of said pair of axial slots so as to secure the probe on the handle in the desired orientation.

17 Claims, 4 Drawing Sheets

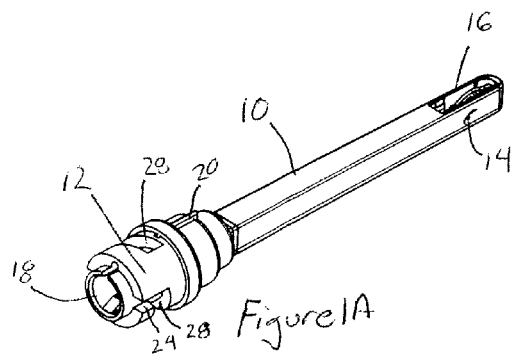
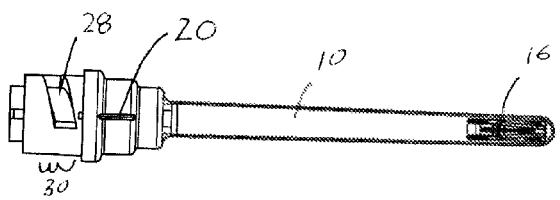
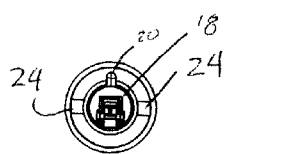
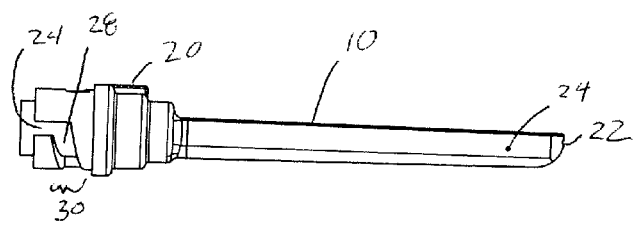
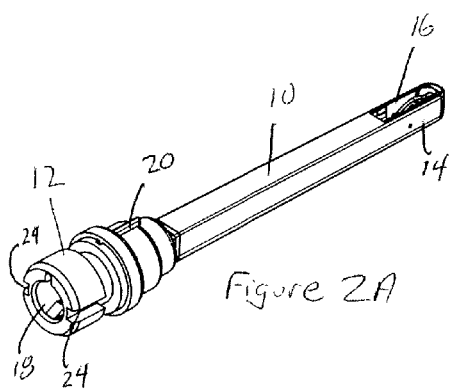
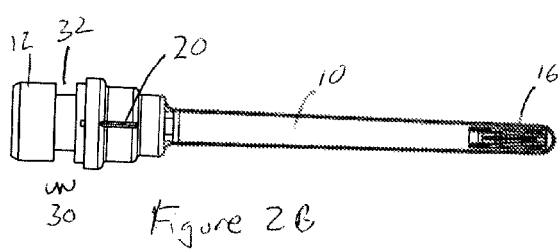
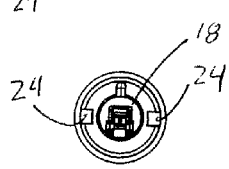
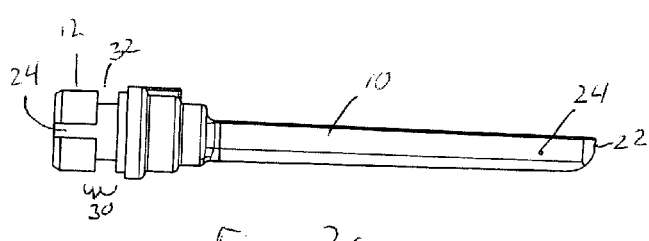

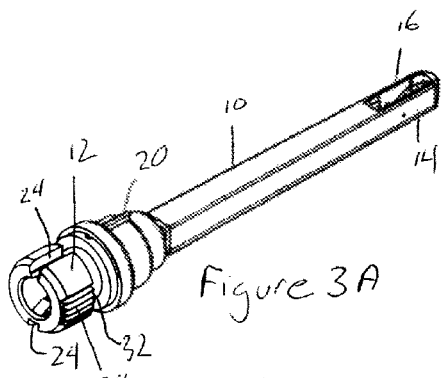
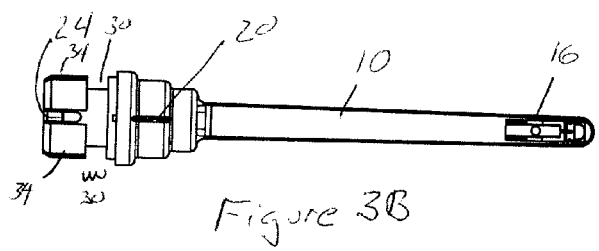
Figure 3A
Figure 3B
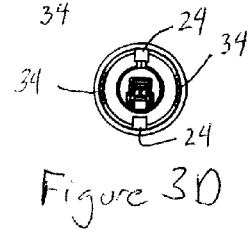
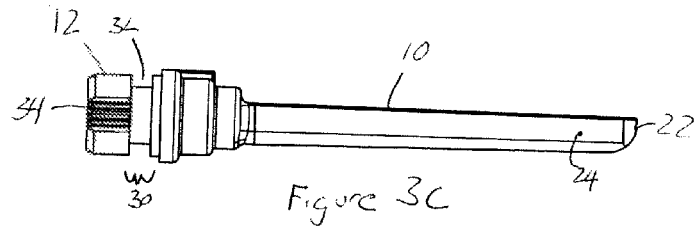
Figure 3D
Figure 3C
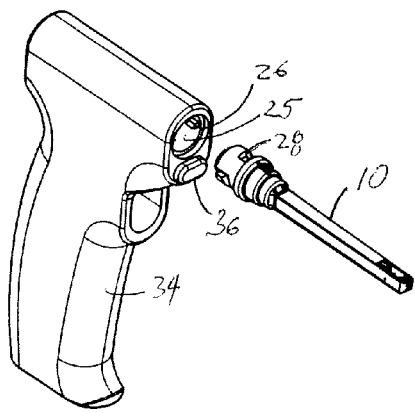
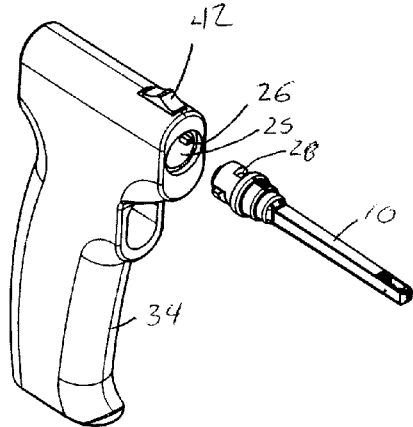
Figure 4A
Figure 4B

HUB AND HANDLE DESIGN FOR CARPAL TUNNEL RELEASE TOOL

BACKGROUND OF THE INVENTION

1. Field of the Invention

The present invention generally relates to surgical instruments used for carpal tunnel release, and is particularly directed to an improved hub and handle design.

2. Background Description

MicroAire Surgical Instruments has been marketing for a number of years a surgical tool based on U.S. Pat. No. 4,962,770 to Agee et al., U.S. Pat. No. 4,963,147 to Agee et al., U.S. Pat. No. 5,089,000 to Agee et al., and U.S. Pat. No. 5,306,284 to Agee et al, each of which is incorporated fully herein by reference. This surgical tool is used to inspect and manipulate selected tissue in a body cavity, and has particular application to performing safe and effective carpal tunnel release. These tools include a handle assembly, a probe member, an optical system, and a cutting system. The optical system and cutting system extend through the handle and into the probe and permit a surgical blade to be selectively deployed and retracted from a lateral opening in the top surface of the probe at its distal end.

The preferred use of the surgical instrument in performing carpal tunnel release is accomplished by forming a short transverse incision located proximal to the carpal tunnel and the wrist flexion crease. After longitudinal spreading dissection, to avoid injury to the sensory nerves, the incision is continued through the deep fascia of the forearm, the distal extension of which leads to the flexor retinaculum. After an incision through the finger flexor synovium, extension of the wrist will then expose the proximal opening of the carpal tunnel, thereby forming a passage to the carpal tunnel. The rotational orientation of the probe relative to the handle or holder is adjustable to suit the needs of the surgeon. After adjusting the rotational orientation of the probe, the probe is inserted through the incision and desirably through the length of the carpal tunnel to the distal edge of the flexor retinaculum.

By employing the optical system, and through manipulation of the patient's extremities, the anatomy within the carpal tunnel can be clearly visualized on a display of a video monitor connected to a video camera and lighting source associated with the optical system. The distal end of probe will desirably have gently displaced the tendons, bursa and median nerve found within the carpal tunnel to facilitate insertion of the probe. Then the lateral aperture of the probe will be positioned adjacent the medial surface of the flexor retinaculum and, desirably, the configuration of the probe upper surface (which is preferably a flat surface) will exclude the displaced tissues from the region surrounding the lateral aperture. Markers can be used to indicate the point on the probe where the blade elevates, and help facilitate proper placement of the probe relative to the distal edge of the flexor retinaculum.

At the appropriate location, a cutting blade will be extended to contact the distal edge of the flexor retinaculum, while the surgeon views the tissue to be divided via the display. The blade point will desirably be extended to a position sufficient to completely release the ligament. While viewing (through the lateral aperture in the probe) the intended path of the extended cutting blade, the probe is then withdrawn, thereby dividing the flexor retinaculum and releasing the carpal tunnel.

The surgical tool described by Agee et al. is safe and effective and well regarded in the surgical community. Improvements to the mechanism for securely fastening the probe to the handle and for orienting the lateral opening of the probe to either side of the handle will be well regarded within the community. Currently, the tool includes a spring loaded knob and locking member which cooperates with an annular groove in the probe end. To align the probe to one side or another, the surgeon must align indicia or a rib member on the probe with indicia on the handle and screw the knob a sufficient amount to tighten the locking member against the probe

SUMMARY OF THE INVENTION

It is therefore an object of this invention to provide an improved hub and handle design for a surgical instrument, such as a carpal tunnel release tool described above in conjunction with the Agee et al. patents (U.S. Pat. Nos. 4,926,770, 4,963,147, 5,089,000, and 5,306,284, each of which are herein incorporated by reference).

According to the invention, the proximal end of a probe is provided with a pair of axial grooves that lead to a slotted twist region, and the handle includes a bore with inwardly projecting land regions sized to fit within the axial grooves and the slotted twist region. This allows the probe to slide within the bore, and then be twisted to its proper orientation. The pair of axial grooves on the probe end also serve the function of interacting with a locking member actuated by a button, slider, or similar device on the handle surface. Once the probe is twisted to the left or the right side of the handle, the locking member will be moved into position in at least one of the axial slots preferably under the influence of a spring bias. This prevents the probe from rotating accidentally during use. In addition, the slotted twist region and inwardly projecting lands of the bore prevent the probe from being removed from the handle accidentally during use. In a variation on the design, the locking member can cooperate with a series of depressions formed in the proximal end of the probe so that the probe can be oriented at a number of discrete angles. The slotted twist region can take a number of different forms including an annular groove in the circumference of the proximal end of the probe, or a pair of slotted pathways that accommodate a partial twist, such as a quarter twist, of the probe (it being understood that the slotted pathways could be sized for different amounts of twisting depending on the tool design). A variety of locking mechanisms can be used including, for example, pushbuttons at the top and front of the handle, or sliders at the top of the handle (it being recognized that the actuators can be positioned at a number of different locations on the handle, and can take a number of different forms). Preferably, the probe is disposable and made of a durable plastic material; however different materials such as composites, glass and metal can be used. Furthermore, to lighten the instrument, it is preferable that the handle be made of a rugged plastic material.

BRIEF DESCRIPTION OF THE DRAWINGS

The foregoing and other objects, aspects and advantages will be better understood from the following detailed description of a preferred embodiment of the invention with reference to the drawings, in which:

FIGS. 1A-1D are isometric, top, side, and end views of a two position screw lock hub design for a probe;

FIGS. 2A-2D are isometric, top, side and end views of a two position twist lock hub design for a probe;

FIGS. 3A-3D are isometric, top, side and end views of an adjustable position twist lock hub design for a probe;

FIGS. 4A-4D are isometric views of probe and handle combinations where FIG. 4A shows the probe of FIG. 1A being inserted into a handle with a button release, FIG. 4B shows the probe of FIG. 1A being inserted into a handle with a slide release, FIG. 4C shows the probe of FIG. 2A being inserted into a handle with a top button release, and FIG. 4D shows the probe of FIG. 3A being inserted into a handle with a top button release;

DETAILED DESCRIPTION

Figure 4C:
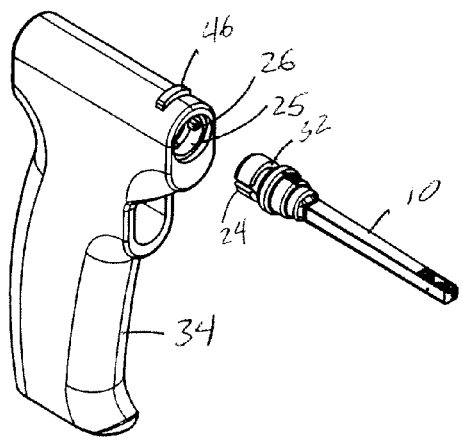

FIGS. 1A-1D and 2A-2D show probe designs where the probe can be selectively locked in a position that is oriented towards the left or right side of a surgical tool handle. FIGS. 3A-3D show a variation on the design shown in FIGS. 2A-2D where the probe can be locked in additional positions to the right and left side orientation. In each of these Figures, like elements use the same numbers. The probe designs primarily differ at the proximal end, as will be discussed in more detail below.

The probe 10 is preferably a disposable item that is attachable to a handle device and its proximal end 12. Its distal end 14 can be inserted into a body cavity, and particularly into incision sites used when performing carpal tunnel release. The probe 10 preferably has a flat top surface that has a lateral opening 16 near the distal end. The lateral opening 16 allows for a cutting blade (not shown) located inside the probe 10 to be selectively deployed to performing cutting at locations selected by the surgeon. After cutting, the cutting blade is fully retractable within the lateral opening. Cutting is performed using an optical system (not shown) that passes through the probe 10 from an opening 18 in its proximal end 12 to the lateral opening 16. The optical system may include optical fibers, optical waveguides, or a series or lenses or other suitable components. Preferably the optical system includes a camera, a display, and other components which allow the surgeon to view the tissue located at the lateral opening 16 using a remotely positioned display device. This enables a surgeon to make cuts at precise locations where tissue manipulation would provide benefit to the patient.

From the top view (FIGS. 1B, 2B, and 3B) it can be seen that a rib 20 can be provided which preferably precisely aligns with the path taken by the cutting blade when it is deployed from the lateral opening 16. While not shown in the figures, markings or other indicia can be advantageously positioned on the top surface of the probe 10 to assist the surgeon in placing the probe in the proper location. While the embodiments shown herein have a single lateral opening 16 in the top surface near the distal end of the probe 10, it should be understood that more than one opening could be provided (e.g., there could be separate openings for the optical system and the blade).

From the side view (FIGS. 1C, 2C, and 3C) it can be seen that the distal end of the probe 10 is closed 22 and preferably has a curved shape. This allows the end of the probe 22 to gently displace the tendons, bursa and median nerve found within the carpal tunnel, thus facilitating insertion of the probe. Pivot pin 24 is shown on the side of the probe 10. The blade is preferably deployed and retracted using a tool extension shaft (not shown) that passes through the probe 10 and cooperates with a pivot pin 24 for pivoting the blade open and closed.

Figure 6:
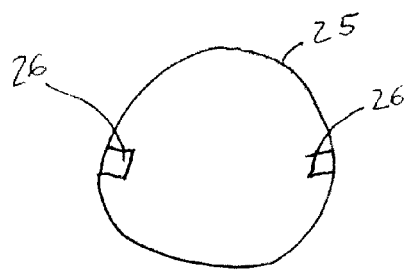
FIG. 6 is a schematic drawing of a bore hole with two inwardly projecting land regions.

From the end view (FIGS. 1D, 2D, and 3D) it can be seen that the proximal end 12 has two axial slots 24 on opposite sides. These slots 24 serve the dual function of guiding the proximal end 12 of the probe 10 into a bore of surgical tool handle and interacting with a locking mechanism, as is discussed in detail below. FIG. 6 schematically shows that the bore 25 of the handle includes inwardly projecting land regions 26. To install the probe on the handle or to remove the probe from the handle, the two axial slots 24 must be aligned with the inwardly projecting land regions 26.

FIGS. 1A-1C show an embodiment of the probe where there are two slotted pathways 28 in the form of a threaded screw partial twist in a slotted twist region 30 of the proximal end 12 of the probe. The two slotted pathways 28 begin just after the two axial slots 24 and are connected therewith. The inwardly projecting lands 26 of the bore 25 (FIG. 6) fit within the two slotted pathways 28 and permit a partial twist similar to a threaded screw. While FIGS. 1A-1C show a ¼ turn twist, it should be understood that pathways of different length and turn radius can be used. The ¼ twist has the advantage of being able to turn the lateral opening 16 of the probe 10 such that it is either facing in the direction of the left side or the right side of the handle.

In contrast, the embodiments shown in FIGS. 2A-2C and 3A-3C show that the slots 24 lead to an annular groove 32 which spans the circumference of the proximal end 12 of the probe 10 at the slotted twist region 30. Similar to the description above for FIGS. 1A-1C, once the inwardly projecting lands 26 of the bore 25 pass through the slots 24 of the probes 10 depicted in FIGS. 2A-2C and 3A-3C, they enter the annular groove 32, thus enabling the probe 10 to be twisted to the left or right.

FIGS. 3A-3D also show the inclusion of a series of depressions 34 in the proximal end 12 of the probe 10. In the embodiment shown in FIGS. 3A-3D, a locking member (discussed below) will be able to extend into each of the depressions 34, as well as each of the slots 24 to lock the probe 10 to a handle of a surgical tool.

Also, by contrasting FIGS. 2A-2D with FIGS. 3A-3D, it can be seen that the location of the slots 24 can vary depending on the design choice of the manufacturer. That is, the slots 24 can be oriented to the sides of the top surface of the probe 10 (FIGS. 2A-2D) or in alignment with the top and bottom surface of the probe (FIGS. 3A-3D) or at any other orientation desired.

FIGS. 4A-4D respectively show probes being inserted into a different handles, and FIGS. 5A-5D show cut away illustrations with probe inserted into and locked to the handle using different locking mechanisms.

With reference to FIG. 4A, a probe 10 is inserted into the bore 25 of a handle 34 which has an actuator 36, in the form of a button, on its front surface. With reference to FIG. 5A, the actuator 36 is spring 38 biased and includes a locking pawl or member 40 which fits within either one of the two slots 24 (best shown in FIGS. 1A, 1C, and 1D) at the proximal end 12 of the probe. In operation, the actuator 36 is depressed and the probe 10 has its proximal end slid into the bore 25. Once the lands 26 have cleared the two axial slots 24, the probe is twisted to have the lateral opening on its top surface face in the direction of either the left side or right side of the handle 34 (note that the lateral opening faces into the paper in FIG. 5A). Then, the actuator is released to cause the locking pawl or member 40 to slide into one of the two axial slots 24. This firmly secures the probe 10 to the handle 34 as the locking pawl or member 40 prevents rotation of the probe 10 within bore 25 of the handle, and the lands 26 within the slotted twist region 30 prevent axial movement of the probe 10 out of the bore 25 in the handle 34. The optical system can be inserted through the housing and into the probe 10 after its installation on the handle 34, and the tool extension shaft can be connected (it being understood that connection of these elements can occur also occur before or during the insertion and twisting of the probe 10). Removal of the probe 10 from the handle 10 occurs in the reverse order by beginning with depressing of the button actuator 36.

An advantage of the design shown in FIGS. 4A and 5A is that the opening can be securely locked in an orientation facing in the same direction as the left or right side of the handle 34 without requiring the surgeon to line up the rib with indicia on the handle. Further, the design allows locking of the probe in place simply by releasing a button actuator and without having to twist a knob for tightening a screw to a point where unintentional rotation of the probe is avoided.

Figure 5A:
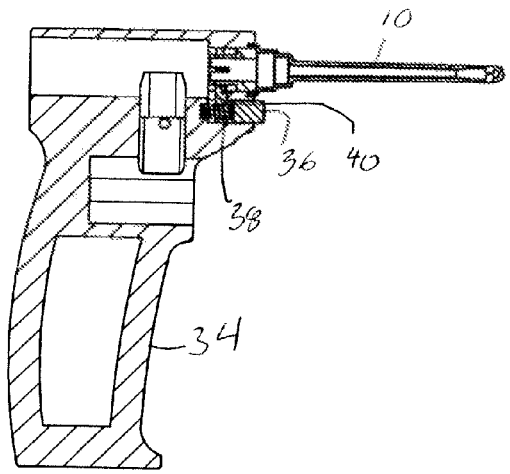
FIGS. 5A-5D are cut away illustrations of the probe and handle combinations of FIGS. 4A-4D where the probe has been inserted into the handle, twisted so that the upper face of the probe is oriented to one side of the handle, and locked in place using a locking mechanism that includes an actuator on the handle.
Figure 5B:
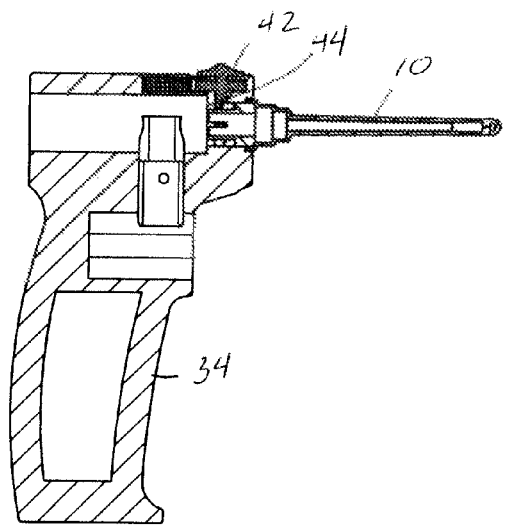

The configuration shown in FIGS. 4B and 5B is similar to that shown in FIGS. 4A and 4B. However, the configuration shown in FIGS. 4B and 5B shows a spring biased slider 42 on the top of the handle 34. The slider 42 could be positioned almost anywhere on the handle. The key feature is that the slider has a locking pawl or member 44 which slides into one of the two axial slots 24 at the proximal end 12 of the probe 10. With the slider 42 arrangement, the spring biasing might not be used. If not, the surgeon would be required to slide the slider into a position where the locking pawl or member 44 fits in an axial slot 24 at the proximal end 12 of the probe 10 when it is desired to secure the probe 10. Attachment and removal of the probe is achieved in the same manner discussed above with respect to FIGS. 4A and 5A.

Figure 5C:
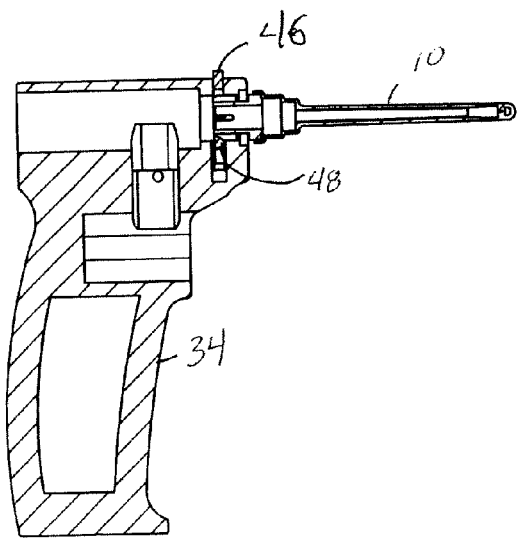

The configuration shown in FIGS. 4C and 5C is similar to that shown in FIGS. 4A and 5A; however, a locking button 46 at the top of the handle 34 is employed. FIGS. 4C and 5C also show a probe similar to that depicted in FIGS. 2A-2D being attached to the handle 34. The locking button 46 is preferably spring biased and includes a locking pawl or member 48 that fits within the axial slots 24 at the proximal end 12 of the probe 10. Attachment and removal of the probe 10 is achieved in the same manner as discussed above with respect to FIGS. 4A and 5A.

Figure 4D:
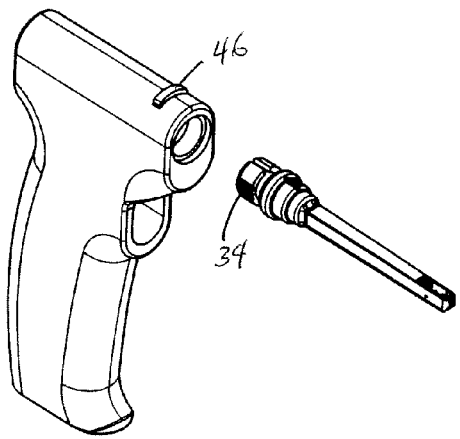
Figure 5D:
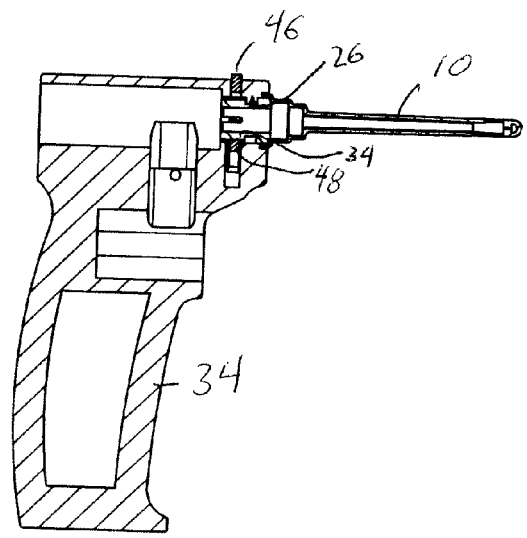

The configuration shown in FIGS. 4D and 5D is similar to that shown in FIGS. 4C and 5C, except that a probe similar to that depicted in FIGS. 3A-3D is being attached to the handle 34, thus, the locking pawl or member 48 fits into one of the depressions in the series of depressions 34 at the proximal end 12 of the probe 10. The inwardly projecting lands 26 are depicted at the top and bottom of the bore in FIG. 5D since the slots 24 in the proximal end of the probe are on the top and bottom as shown in FIGS. 3A-D. The configuration shown in FIGS. 4D and 5D allows for a surgical tool to have the lateral opening 16 of the probe positioned at a number of different orientations (as opposed to being positioned only facing the left or the right side).

Figure 7:
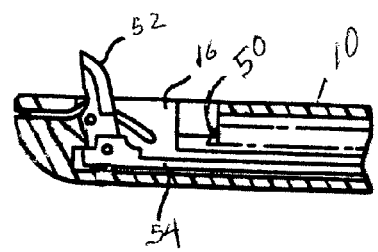
FIG. 7 shows an example of a retractable cutting blade and optical system positioned within a probe.

There are a number of cutting tool operating mechanism and optical system 10 can be inserted into the probe 10 (see for example U.S. Pat. Nos. 4,962,770, 4,963,147, 5,089,000, and 5,306,284, each of which is incorporated by reference). FIG. 7 shows one example where an optical system 50 extends within the probe 10 to the lateral opening 16. A cutting blade 52 is selectively deployed or retracted using the tool extension shaft 54. This and other configurations can be used within the practice of this invention.

While the invention has been described in terms of its preferred embodiments, those skilled in the art will recognize that the invention can be practiced with modification within the spirit and scope of the appended claims.

Having thus described my invention, what I claim as new and desire to secure by Letters Patent is as follows:

1. A surgical instrument for cutting selected tissue in a body cavity while under visual inspection, comprising:
    a probe having a closed distal end, an open proximal end, and an axial passage extending from said proximal end to said distal end through which at least an optical system and tool extension shaft extend, said probe having an upper surface with a lateral aperture positioned near said distal end through which a cutting blade can be extended and retracted under operation of said tool extension shaft,
    wherein said proximal end includes a connector section with two axial slots on opposite sides of said proximal end and a slotted twist region, wherein said slotted twist region includes two slotted pathways in the form of a threaded screw partial twist where said slotted pathways begin at a distal end of said two axial slots and are connected therewith;
    a handle having a top region and a lower grip region and a left and right side, said top region including a bore for receiving said proximal end of said probe, said bore including two inwardly projecting land regions positioned on opposite sides of said bore, said two inwardly projecting land regions fitting within said two axial slots and said slotted twist region of said proximal end of said probe,
    wherein said two inwardly projecting land regions in said bore of said handle and said two axial slots and said slotted twist region of said proximal end of said probe being configured to permit said probe to be attached to and removed from said handle by sliding said proximal end of said probe into said bore of said handle with said two inwardly projecting land regions passing through said two axial slots and said two slotted pathways by sliding said proximal end of said probe into said bore and twisting said probe such that said upper surface of said probe is oriented towards said left or right side of said handle with said two inwardly projecting land regions reaching an end of said two slotted pathways; and
    a locking mechanism affixed to said handle which includes a locking member that is selectively movable within said bore of said handle by an actuator positioned on an outer surface of said handle,
    wherein said locking member is moveable into and out of each of said two axial slots at said proximal end of said probe to alternatively lock or unlock said probe to or from said bore of said handle.

2. The surgical instrument of claim 1 wherein said actuator of said locking mechanism is a push button.

3. The surgical instrument of claim 1 wherein said actuator of said locking mechanism is a slider.

4. The surgical instrument of claim 1 wherein said handle and said probe are each made of a plastic material, said plastic material may be the same or different for each of said handle and said probe.

5. The surgical instrument of claim 1 wherein said threaded screw partial twist is ¼ turn twist.

6. A surgical instrument for cutting selected tissue in a body cavity while under visual inspection, comprising:
    a probe having a closed distal end, an open proximal end, and an axial passage extending from said proximal end to said distal end through which at least an optical system and tool extension shaft extend, said probe having an upper surface with a lateral aperture positioned near said distal end through which a cutting blade can be extended and retracted under operation of said tool extension shaft, wherein said proximal end includes a connector section with two axial slots on opposite sides of said proximal end and a slotted twist region, said two axial slots being connected to said slotted twist region, and a plurality of depressions in a periphery of said proximal end of said probe between said two axial slots;

a handle having a top region and a lower grip region and a left and right side, said top region including a bore for receiving said proximal end of said probe, said bore including two inwardly projecting land regions positioned on opposite sides of said bore, said two inwardly projecting land regions fitting within said two axial slots and said slotted twist region of said proximal end of said probe, wherein said two inwardly projecting land regions in said bore of said handle and said two axial slots and said slotted twist region of said proximal end of said probe being configured to permit said probe to be attached to and removed from said handle by sliding said proximal end of said probe into said bore of said handle with said two inwardly projecting land regions passing through said two axial slots and by twisting said probe such that said upper surface of said probe is oriented towards said left or right side of handle with said two inwardly projecting land regions sliding within said slotted twist region; and a locking mechanism affixed to said handle which includes a locking member that is selectively movable within said bore of said handle by an actuator positioned on an outer surface of said handle, wherein said locking member is alternatively moveable into and out of each of said two axial slots and each of said depressions at said proximal end of said probe to alternatively lock or unlock said probe to or from said bore of said handle.

7. The surgical instrument of claim 6 wherein said slotted twist region on said proximal end of said probe is an annular slot in the circumference of said proximal end of said probe.

8. The surgical instrument of claim 6 wherein said actuator of said locking mechanism is a push button.

9. The surgical instrument of claim 6 wherein said actuator of said locking mechanism is a slider.

10. The surgical instrument of claim 6 wherein said handle and said probe are each made of a plastic material, said plastic material may be the same or different for each of said handle and said probe.

11. A surgical instrument for cutting selected tissue in a body cavity while under visual inspection, comprising:

a probe having a closed distal end, an open proximal end, and an axial passage extending from said proximal end to said distal end through which at least an optical system and tool extension shaft extend, said probe having an upper surface with a lateral aperture positioned near said distal end through which a cutting blade can be extended and retracted under operation of said tool extension shaft, wherein said proximal end includes a connector section with two axial slots on opposite sides of said proximal end and a slotted twist region, said two axial slots being connected to said slotted twist region;

a handle having a top region and a lower grip region and a left and right side, said top region including a bore for receiving said proximal end of said probe, said bore including two inwardly projecting land regions positioned on opposite sides of said bore, said two inwardly projecting land regions fitting within said two axial slots and said slotted twist region of said proximal end of said probe, wherein said two inwardly projecting land regions in said bore of said handle and said two axial slots and said slotted twist region of said proximal end of said probe being configured to permit said probe to be attached to and removed from said handle by sliding said proximal end of said probe into said bore of said handle with said two inwardly projecting land regions passing through said two axial slots and by twisting said probe such that said upper surface of said probe is oriented towards said left or right side of handle with said two inwardly projecting land regions sliding within said slotted twist region; and a locking mechanism affixed to said handle which includes a locking member that is selectively movable within said bore of said handle by an actuator positioned on an outer surface of said handle, wherein said locking member is at least alternatively moveable into and out of each of said two axial slots at said proximal end of said probe to alternatively lock or unlock said probe to or from said bore of said handle, said locking member moving on a pathway which is either perpendicular to each of said two axial slots, or which is parallel to said axial slots beginning from a position past said proximal end of said probe.

12. The surgical instrument of claim 11 further comprising a plurality of depressions in a periphery of said proximal end of said probe between said two axial slots, wherein said locking member of said locking mechanism can be moved into and out of each of said plurality of depressions to alternatively lock or unlock said proximal end of said probe to or from said bore of said handle.

13. The surgical instrument of claim 11 wherein said slotted twist region on said proximal end of said probe is an annular slot in the circumference of said proximal end of said probe.

14. The surgical instrument of claim 11 wherein said slotted twist region on said proximal end of said probe includes two slotted pathways in the form of a threaded screw partial twist.

15. The surgical instrument of claim 11 wherein said actuator of said locking mechanism is a push button.

16. The surgical instrument of claim 11 wherein said actuator of said locking mechanism is a slider.

17. The surgical instrument of claim 11 wherein said handle and said probe are each made of a plastic material, said plastic material may be the same or different for each of said handle and said probe.

* * * * *